(12) United States Patent
Magnusson et al.

(10) Patent No.: US 6,746,440 B2
(45) Date of Patent: Jun. 8, 2004

(54) METHOD AND DEVICE FOR KEEPING INFUSION FLUIDS WARM

(76) Inventors: Anders Magnusson, Smedjevägen 4, Krokom (SE), 835 31; Eva Magnusson, Smedjevägen 4, Krokom (SE), 835 31

( * ) Notice: Subject to any disclaimer, the term of this patent is extended or adjusted under 35 U.S.C. 154(b) by 174 days.

(21) Appl. No.: 09/978,627

(22) Filed: Oct. 18, 2001

(65) Prior Publication Data

US 2002/0045857 A1 Apr. 18, 2002

(30) Foreign Application Priority Data

Oct. 18, 2000 (SE) ................................. 0003769

(51) Int. Cl.[7] .............................................. A61M 31/00

(52) U.S. Cl. ...................... 604/500; 604/403; 604/174; 604/113

(58) Field of Search ................................. 604/113, 408, 604/114, 403, 174, 179, 180; 607/104, 96, 112; 165/136; 5/481; 206/545; 602/62

(56) References Cited

U.S. PATENT DOCUMENTS

| 4,573,447 A | * | 3/1986 | Thrash et al. .................. 44/251 |
| 4,804,367 A | * | 2/1989 | Smith et al. ................. 604/113 |
| 4,934,336 A | | 6/1990 | White |
| 5,044,031 A | * | 9/1991 | Sherwood et al. ............. 2/69.5 |
| 5,125,900 A | * | 6/1992 | Teves .......................... 604/114 |
| 5,295,964 A | * | 3/1994 | Gauthier ..................... 604/113 |
| 5,501,338 A | * | 3/1996 | Preston ........................ 206/545 |
| 5,601,894 A | * | 2/1997 | Maruschak ................. 428/36.9 |
| 5,728,147 A | * | 3/1998 | Thomas ....................... 607/112 |
| 6,149,617 A | * | 11/2000 | McNally et al. .............. 602/62 |

FOREIGN PATENT DOCUMENTS

GB 2 248 106 A 3/1992

* cited by examiner

*Primary Examiner*—Brian L. Casler
*Assistant Examiner*—Cris L. Rodriguez
(74) *Attorney, Agent, or Firm*—Young & Thompson

(57) ABSTRACT

A method and device for keeping infusion fluids warm in which not only an infusion bag but also a tube extending from this and a cannula attached to the end of the tube are surrounded by a continuous heat-insulating cover, which heat-insulating person into whom the cannula is inserted.

20 Claims, 1 Drawing Sheet

FIG. 1
FIG. 2
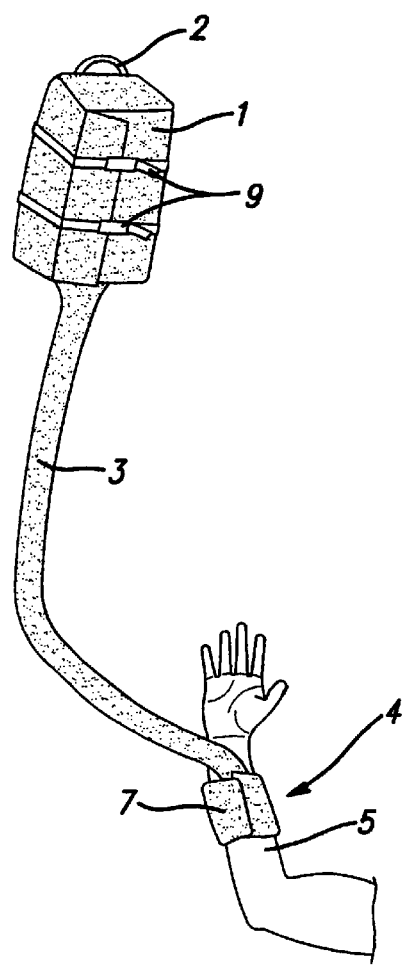
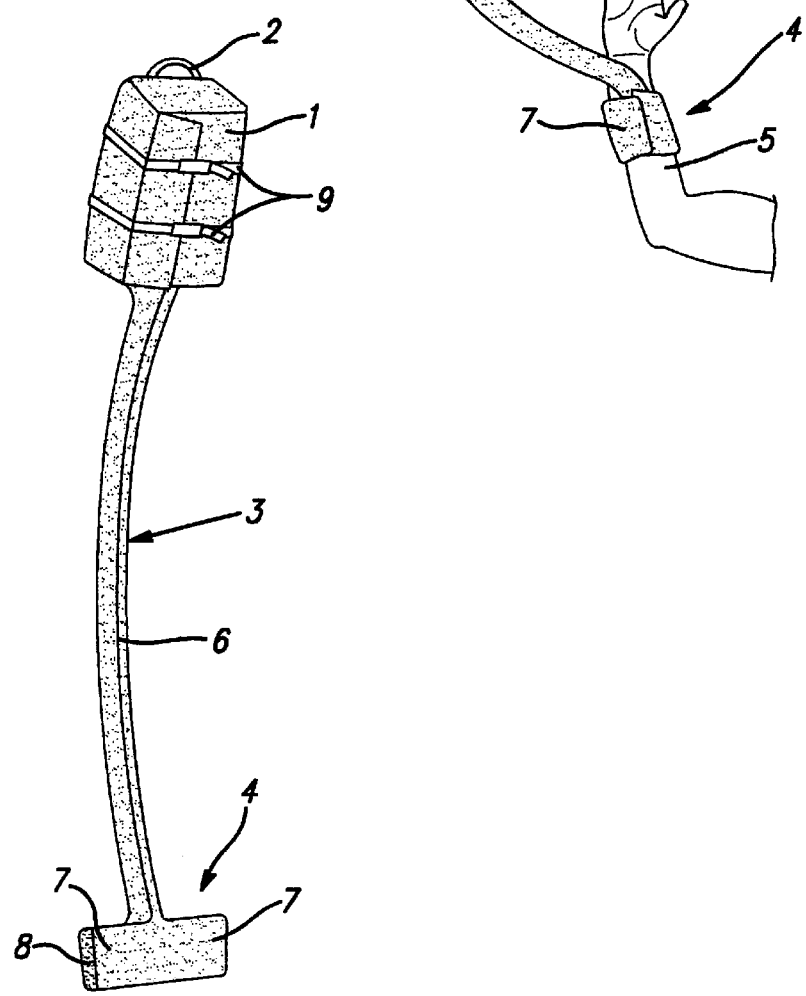

METHOD AND DEVICE FOR KEEPING INFUSION FLUIDS WARM

BACKGROUND OF THE INVENTION

The present invention concerns a method for keeping infusion fluids and similar warm, particularly for outdoor use, for example at the scene of an accident. The invention also concerns a device for execution of the method according to the invention.

DESCRIPTION OF THE RELATED ART

It is well known that fluids that are to be given to persons by infusion should be kept at a temperature as close to body temperature as possible, in order to minimise discomfort and risks. It may be necessary on many occasions to give such fluids to persons who have suffered an accident, and thus it follows that it should be possible to transport the fluids to the site of an accident, and it should be possible there to give them to the person while maintaining the temperature of the infusion fluid. Special bags, for example, have been developed for this purpose that, with the aid of power from, for example, a car in which the fluid has been transported, can maintain the temperature of the contents, such as, for example, an infusion bag at a constant level, for example, approximately 37° C. It has also been realised that it may be necessary during the infusion to enclose the infusion bag in a heat-insulating cover, in order for the infusion bag to maintain its original temperature, or at least, for it not to cool too quickly.

Despite the measures that have been taken in an attempt to be able to maintain the original temperature of the infusion fluid, major problems remain in maintaining the temperature of the infusion fluid up until injection into the person who is to receive the infusion. Naturally, these problems become more severe the lower the ambient temperature is, and these problems may become very severe particularly in winter in the Nordic climate with acute cold and, furthermore, accompanying wind, making the cooling of the infusion fluid even more rapid once the fluid has been taken from its original heated container.

SUMMARY OF THE INVENTION

One aim of the invention thus is to achieve a new method by which the problems mentioned above can be solved, such that infusion fluids can be given to patients without further discomfort or risks, no matter what the weather.

The above-mentioned aim of the invention is achieved with a method for keeping infusion fluids warm in which not only the infusion bag but also the tube that extends from it and a cannula that is attached to the end of the tube are surrounded by a continuous heat-insulating cover, which heat-insulating cover is arranged also to surround that part of a person, for example, one of the arms, into which the cannula is to be inserted.

A further aim of the invention is to achieve a device for keeping an infusion fluid warm with which the above-mentioned problems can be solved, such that infusion fluids can be given to patients without any further discomfort or risks, no matter what the weather.

This further aim of the invention is achieved with a device that comprises a continuous cover manufactured from a heat-insulating material with an upper part for surrounding an infusion bag, a central part for surrounding a tube that runs from the infusion bag, and a lower part for surrounding not only a cannula at the end of the tube, but also that part of the person into which the cannula is to be inserted.

BRIEF DESCRIPTION OF THE DRAWINGS

The invention will now be described in more detail in the form of an embodiment, illustrated with the aid of the attached drawings, in which FIG. 1 shows a schematic view in perspective of a device for keeping an infusion bag warm arranged for use with a person, to one arm of whom the device is attached, and FIG. 2 shows an equivalent view in perspective of the device on its own with the attachment section open.

DESCRIPTION OF THE PREFERRED EMBODIMENTS

The device shown in FIG. 1 is a heat-insulating cover made principally from a textile material, and it demonstrates an upper part 1, which it is appropriate to provide with a hanging means 2. The upper part 1 has been designed such that it can accommodate an infusion bag and totally enclose it. An extended thin central part 3 is attached to the upper part 1 of the device, which has been designed such that it can surround a tube that extends from the infusion bag along its complete length. A lower part 4 is attached to the end of the central part 3 that is opposite to the upper part, which lower part has been designed such that it can completely surround not only the cannula that is placed at the end of the infusion tube, but also the arm 5 of the person into whom it is intended to inject the infusion fluid in the infusion bag.

As has been mentioned, it is appropriate that the heat-insulating cover is manufactured from a textile material, with a outer fabric that resists tearing and is not permeable to water, preferably one that is able to "breathe". Furthermore, the cover has a thick layer of heat-insulating material inside of the outer fabric, and it is then appropriate that it has an inner fabric, of, for example, cotton, inside of this. It is appropriate that it should be possible to open the cover along the complete extent of its length, preferably with the aid of hook-and-loop tape, which makes it easy to open and close the cover for inserting the infusion bag and the associated tube into it. FIG. 2 demonstrates clearly the line 6 of opening, along which the complete cover can be opened in the manner described above. The cover is constructed in one complete piece, intended to cover one infusion bag, the tube associated with it, the cannula at the other end of the tube and the part of the body of the person into whom the cannula has been inserted.

The lower part 4 is attached, as has been described above, to the lower end of the central part 3, and it is provided, as FIG. 2 makes clear, with two flaps 7 that protrude to the side, and which are made from a heat-insulating textile material in the same way as the rest of the cover. These flaps 7 are dimensioned such that they can be placed around and thus surround the arm 5 of the person on whom the device according to the invention is being applied. As is also suggested in FIG. 2, a hook-and-loop tape 8 is arranged on the tabs 7 such that these can be placed around the arm of a person and closed against each other in the manner shown in FIG. 1, and where the flaps 7 thus enclose the arm 5 of the person and also the cannula at the end of the tube that runs inside of the cover from the infusion bag at its upper part 1.

The upper part 1 of the device, or cover, is designed to accommodate not only an infusion bag but also one or more heat bags. It is preferable that these heat bags contain a special mixture of different metals, which, following the addition of a small quantity of water, develops heat, and preferably the heat bag that is marketed by "HJÄLP & R ÄDDNINGs produkter i Norden AB", Järpen, Sweden, under the name "HEAT BAG", for example, the model designated HB 500.

With a system consisting of a heat bag, a heat-insulating cover according to the invention and heat bags, the heat in the infusion fluid can be maintained for the complete journey from the heating that the infusion fluid has received before being placed into the heat-insulating cover up until the injection into the person who is to receive the infusion fluid. In the absence of wind and at temperatures down to approximately +20° C. the temperature of the infusion fluid can normally be maintained with the aid of the heat-insulating cover without the aid of a heat supply. At temperatures from approximately +20° C. and down to approximately −10° C. to −20° C., it may be necessary to insert a heat bag together with the infusion bag in the upper part 1 of the cover, and at temperatures lower than this, two heat bags may be necessary in order to maintain the correct temperature of the infusion fluid. The number of heat bags that must be used, if any, naturally depends on the ambient conditions, the thickness of the heat insulation and the capacity of the heat bags. This can be determined empirically for different types of cover and heat bag, and can be specified, for example, in the form of a table for different temperatures, wind effects and the speed at which infusion takes place.

The speed at which infusion takes place can be influenced from outside of the cover with the aid of tension straps 9 arranged around the upper part, with which the pressure on the infusion bag can be changed such that it is not necessary to open the heat-insulating cover in order to obtain access to, for example, a clamp on the tube.

With the aid of the method and the device according to the invention, it is possible to achieve an infusion system that can be used over the complete range of temperature from +20° C. to −36° C., and in this way it is always possible to be able to inject a fluid with a temperature of approximately +37°C.

What is claimed is:

1. A method for keeping infusion fluids warm, characterised in that not only an infusion bag but also a tube that extends from it and a cannula attached to the end of the tube are surrounded by a continuous heat-insulating cover (1,3, 4), which heat-insulating cover is arranged such that it also surrounds that part of a person (5) into whom the cannula is inserted.

2. The method according to claim 1, characterised in that one or more heat bags are inserted into that part of the cover (1) in which the infusion bag is located.

3. The method according to claim 1, characterised in that the speed at which the fusion is carried out can be changed with the aid of tension straps (9) that can be tensioned over the infusion bag from the outside.

4. The method according to claim 1, wherein the cover (1,3,4) can be easily opened and closed with the aid of hook-and-loop tape.

5. A device of keeping infusion fluids warm, comprising:
a continuous cover manufactured from a heat-insulating material with an upper part (1) shaped for enclosure of an infusion bag, an elongated central part (3), when closed, being tube-shaped and for enclosure of a tube that stretches from the infusion bag, and a lower part (4) for enclosure not only of a cannula at the end of the tube but also that part of a person (5) into whom the cannula is inserted, the central part and the lower part being in an inverted T shape when the lower part is in an open configuration.

6. The device according to claim 5, characterised in that the heat-insulating cover (1,3,4) can be opened and closed along its entire length with the aid of hook-and-loop tape (6).

7. The device according to claim 5, characterised in that the lower part (4) of the heat-insulating cover is provided with flaps (7) that protrude to the side designed to be able to surround a part of the body (5) of a person.

8. The device according to claim 5, wherein the upper part (1) of the heat-insulating cover is designed to be able to accommodate not only the infusion bag but also one or more heat bags.

9. The device according to claim 8, characterised in that the upper part (1) of the heat-insulating cover is provided on its outer surface with tension straps (9) with which pressure can be applied onto the infusion bag from the outside.

10. An infusion fluid assembly covering device for keeping an infusion fluid warm, comprising:
a heat-insulating cover,
the cover comprising an upper part (1), the upper part, when closed, in the shape of an infusion bag and sized to totally enclose the infusion bag,
the cover comprising an elongate central part (3) attached to the upper part and, when closed, in the shape of a tube so as to be enclosable along a length of the tube,
the cover comprising a lower part (4) attached to an end of the central part and shaped to completely surround a cannula placed at the end of the tube and to surround an the arm (5) of a person.

11. The device of claim 10, wherein the cover is made from a textile material.

12. The device of claim 11, wherein the cover comprises an outer surface material that is non-permeable to water.

13. The device of claim 12, wherein the cover further comprises a layer of heat-insulating material inside of the outer surface material.

14. The device of claim 13, wherein the cover further comprises an inner fabric.

15. The device of claim 10, further comprising an opening extending from the lower part, along the length of the central part, and along the upper part.

16. The device of claim 15, wherein the opening comprises hook-and-loop tape.

17. The device of claim 10, wherein the lower part comprises two flaps (7) so that, when in an open configuration, the central part and the lower part together form an inverted T shape.

18. The device of claim 10, further comprising a heat bag, and wherein the upper part further comprises interior space accommodating, in addition to the infusion bag, the heat bag.

19. The device of claim 10, wherein the upper part further comprises tension straps (9) arranged around the upper part, the tension straps being orthogonal to an elongate length of the central part.

20. The device of claim 10, wherein,
the upper part comprises a hanging element (2), and
the cover comprises an outer surface layer that is non-permeable to water, an intermediate layer of heat-insulating material inside of the outer surface material, and an inner cotton fabric layer.

* * * * *